US010570443B2

(12) United States Patent
Schutz et al.

(10) Patent No.: US 10,570,443 B2
(45) Date of Patent: Feb. 25, 2020

(54) METHODS OF QUANTIFYING CELL-FREE DNA

(71) Applicant: Chronix Biomedical, San Jose, CA (US)

(72) Inventors: Ekkehard Schutz, Gottingen (DE); Julia Beck, Gottingen (DE)

(73) Assignee: Chronix Biomedical, San Jose, CA (US)

(*) Notice: Subject to any disclaimer, the term of this patent is extended or adjusted under 35 U.S.C. 154(b) by 0 days.

(21) Appl. No.: 15/516,014

(22) PCT Filed: Sep. 30, 2015

(86) PCT No.: PCT/US2015/053304
§ 371 (c)(1),
(2) Date: Mar. 30, 2017

(87) PCT Pub. No.: WO2016/054255
PCT Pub. Date: Apr. 7, 2016

(65) Prior Publication Data
US 2017/0327869 A1 Nov. 16, 2017

Related U.S. Application Data

(60) Provisional application No. 62/058,261, filed on Oct. 1, 2014.

(51) Int. Cl.
*C12Q 1/68* (2018.01)
*C12Q 1/686* (2018.01)

(52) U.S. Cl.
CPC .................................. *C12Q 1/686* (2013.01)

(58) Field of Classification Search
None
See application file for complete search history.

(56) References Cited

U.S. PATENT DOCUMENTS

2012/0108460 A1* 5/2012 Quake .................. C12Q 1/6881
506/9

FOREIGN PATENT DOCUMENTS

WO 2012/058316 A1 5/2012

OTHER PUBLICATIONS

Hindson et al. (Analytical Chemistry, 2011, 83:8604-8610) (Year: 2011).*
Lui et al. (Clinical Chemistry, 2002, 48:3, p. 421-427) (Year: 2002).*
Barrett et al. (Clin Chem, 2012, 58:6, p. 1026-1032) (Year: 2012).*
Beck, J et al. Digital Droplet PCR for Rapid Quantification of Donor DNA in The Circulation of Transplant Recipients as a Potential Universal Biomarker of Graft Injury. Clinical Chemistry 2013, vol. 59, No. 12, pp. 1732-1741.
Lun, Fmf et al. Noninvasive Prenatal Diagnosis of Monogenic Diseases by Digital Size Selection and Relative Mutation Dosage on DNA in Maternal Plasma. PNAS. Dec. 16, 2008, vol. 105, No. 50, pp. 19920-19925.

(Continued)

*Primary Examiner* — Stephanie K Mummert
(74) *Attorney, Agent, or Firm* — Kilpatrick Townsend & Stockton LLP

(57) ABSTRACT

This invention provides a method of quantifying chimeric DNA in a cell-free DNA sample.

8 Claims, 5 Drawing Sheets

(56) References Cited

OTHER PUBLICATIONS

Sikora, A et al. Detection of Increased Amounts of Cell-Free Fetal DNA With Short PCR Amplicons. Clinical Chemistry. 2010, vol. 56, No. 1, pp. 136-138.
International Search Report from PCT/US2015/53304 dated Dec. 28, 2015, 3 pages.
Supplementary European Search Report, EP Application No. EP 15 84 8055, dated Mar. 14, 2018, 9 pages.
Didelot, et al., "Multiplex Picoliter-Droplet Digital PCR for Quantitative Assessment of DNA Integrity in Clinical Samples," Clinical Chemistry, 59:5, Feb. 12, 2013, pp. 815-823.
Taly, et al., "Multiplex Picodroplet Digital PCR to Detect KRAS Mutations in Circulating DNA from the Plasma of Colorectal Cancer Patients," Clinical Cancer, 59:12, Aug. 12, 2013, pp. 1722-1731.
Whale, et al., "Methods for Applying Accurate Digital PCR Analysis on Low Copy DNA Samples," Plos One, vol. 8, No. 3, Mar. 5, 2013, 10 pages.

\* cited by examiner

METHODS OF QUANTIFYING CELL-FREE DNA

CROSS REFERENCE TO RELATED APPLICATIONS

This application claims benefit of U.S. Provisional Application No. 62/058,261, filed Oct. 1, 2014, which application is herein incorporated by reference.

BACKGROUND OF THE INVENTION

The quantification of traces of chimeric cell-free DNA (cfDNA), i.e., (cfDNA that comprises normal genomic DNA from a patient and DNA from another individual or DNA from patient tissue or cells that differ from normal genomic DNA) is useful as a diagnostic maker in cancer, solid organ transplantation and fetal aneuploidy. However, compared to other established biochemical tests, standardization suffers from obstacles, such as low concentrations and fragmentation of cfDNA. Digital PCR enables a high precision in quantification, but thorough error control is needed for reliable measurements. This invention addresses the need for improved quantification for digital PCR methods that assess chimeric cf DNA.

BRIEF SUMMARY OF THE INVENTION

Certain aspects of the invention are summarized below. The invention is not limited to the particular embodiments described in this summary.

In one aspect, the invention provides a method of estimating the proportion of DNA in a cfDNA sample that is amplifiable in a PCR reaction, the method comprising:
(a) providing a cell-free DNA (cfDNA) sample from a blood, serum or plasma sample obtained from a patient;
(b) performing a multiplex digital PCR comprising at least a first amplification and a second amplification, wherein the first amplification targets a first single copy genomic locus and results in production of a first amplicon a second amplification targets a second single copy genomic locus and results in production of a second amplicon, wherein the first and second amplicon differ in length by at least 50 base pairs;
(c) determining the proportion of the first or second amplicon in the total amplified product from the digital PCR of step (b) to provide a correction factor for the amplifiable fraction of the cfDNA sample, and
(d) correcting a diagnostic digital PCR performed on the cfDNA sample to evaluate the level of chimeric DNA present in the sample using the correction factor determined in step (c).

In some embodiments, step (b) further comprises an amplification reaction that targets DNA that was added to the blood, serum, or plasma sample prior to extraction. In some embodiments, the first and second amplicons differ in length by 100 nucleotides or more. In some embodiments, the longer of the two amplicons is from 150 to 600 base pairs in length, or from 150 to 400 base pairs in length, and the shorter of the two amplicons is from 50 to 150 base pairs in length.

The cfDNA samples can be from any number of patients. In some embodiments, the cfDNA sample is from a transplant patient, a cancer patient, or a pregnant patient. In typical embodiments, the patient is a human.

DETAILED DESCRIPTION OF THE INVENTION

Figure 1:
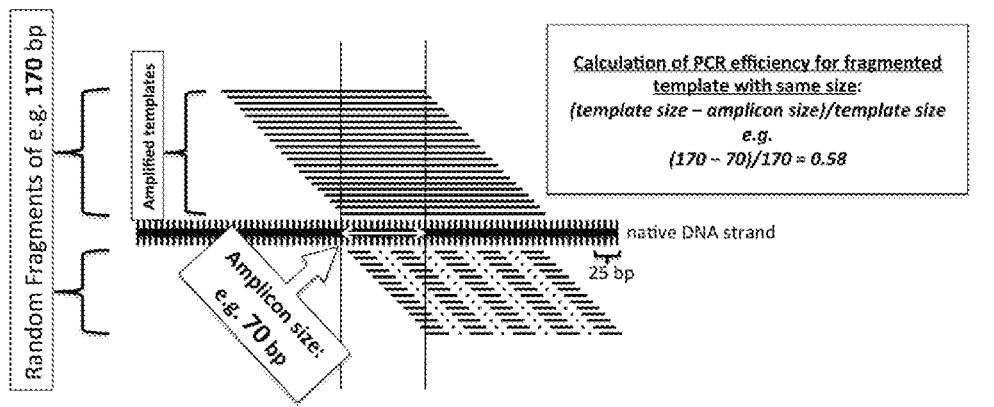
FIG. 1: Upper panel: Schematic drawing of PCR decrease of amplifiable fraction (θAmp) caused by random fragmentation of the template, given that all fragments are of exactly the same size. Lower panel: Correction factor estimation for θAmp based on the fragment length profile of cfDNA. The dashed line (AUC) is the real amount, other lines depict the cumulative efficiency over the length distribution, where the maximum value is the factor for the amplicon that can be used for correction
Figure 1:
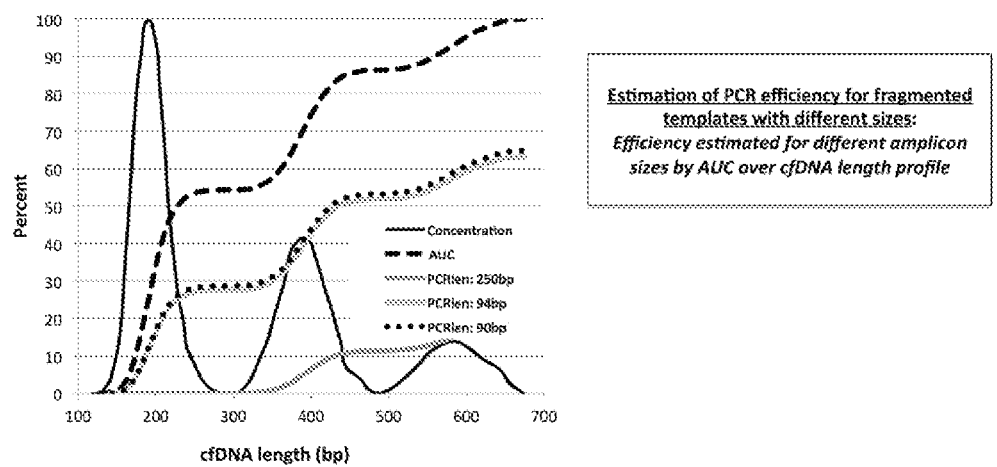

The term "cell-free DNA" or "cfDNA" as used herein means free DNA molecules of 25 nucleotides or longer that are not contained within any intact cells. In the context of the current invention, "cfDNA" is typically evaluated in human blood, e.g., can be obtained from human serum or plasma.

The term "chimeric" or "mosaic" in the context of cfDNA is used herein to refer to cfDNA in a patient that comprises normal DNA and DNA that is not normal to the patient, i.e., the DNA is from another individual, such as a transplant donor or fetal DNA; or is from the patient, but not from a normal tissue, e.g., DNA from cancer cells.

Generally, cfDNA is fragmented. For example, three distinct peaks are regularly observed in human cfDNA resembling the first three shortest moieties of apoptotic DNA fragmentation. As used herein, the "proportion of amplifiable DNA" or "fraction of amplifiable DNA" in a cfDNA sample refers to the amount of DNA in a sample that can provide an amplified product of a size of interest, as a fraction of the total present DNA of the same region that could be amplified if no fragmentation was present.

A "graft" as used herein refers to tissue material, from a donor that is transplanted into a recipient. For example, a graft may be from liver, heart, kidney, or any other organ.

The term "primer" refers to an oligonucleotide that acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer includes a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5' end of the primer that hybridizes to a capture oligonucleotide.

The term "probe" refers to an oligonucleotide that selectively hybridizes to a target nucleic acid under suitable conditions. A probe for detection of the biomarker sequences described herein can be any length, e.g., from 15-500 bp in length. Typically, in probe-based assays, hybridization probes that are less than 50 bp are preferred.

The term "target sequence" or "target region" refers to a region of a nucleic acid that is to be analyzed and comprises the sequence of interest, e.g., a region containing a SNP biomarker.

As used herein, the terms "nucleic acid," "polynucleotide" and "oligonucleotide" refer to primers, probes, and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA. Oligonucleotides for use in the invention may be used as primers and/or probes.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, N6-methyladenine, N6-tert-butyl-benzyl-adenine, imidazole, substituted imidazoles, 5-fluorouracil, 5 bromouracil, 5-chlorouracil, 5-iodouracil, hypoxanthine, xanthine, 4-acetylcytosine, 5 (carboxyhydroxymethyl)uracil, 5 carboxymethylaminomethyl-2-thiouridine, 5 carboxymethylaminomethyluracil, dihydrouracil, beta-D-galactosylqueosine, inosine, N6 isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2 thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785, each of which is incorporated herein by reference in its entirety. Furthermore, a nucleic acid, polynucleotide or oligonucleotide can comprise one or more modified sugar moieties including, but not limited to, arabinose, 2-fluoroarabinose, xylulose, and a hexose.

"Repetitive sequences" refer to highly repeated DNA elements present in a genome. These sequences are usually categorized in sequence families and are broadly classified as interspersed repetitive DNA (see, e.g., Jelinek and Schmid, Ann. Rev. Biochem. 51:831-844, 1982; Hardman, Biochem J. 234:1-11, 1986; and Vogt, Hum. Genet. 84:301-306, 1990) or tandemly repeated DNA. Repetitive elements include satellite, minisatellite, and microsatellite DNA. In humans, interspersed repetitive DNA includes Alu sequences, short interspersed nuclear elements (SINES) and long interspersed nuclear elements (LINES), and endogenous retroviruses (ERVs). The categorization of repetitive elements and families of repetitive elements and their reference consensus sequences are defined in public databases (e.g., repbase (version 12.09)—Genetic Information Research Institute (Jurka et al., *Cytogenet Genome Res* 2005; 110:462-7)).

A "unique sequence" as used herein is a sequence that is free of repeated DNA that can be localized to a single site on a genome. A "unique" sequence in the context of this invention is equivalent to a single-copy sequence.

As used herein, the singular forms "a," "an" and "the" include plural referents unless the context clearly dictates otherwise. Thus, for example, reference to "a molecule" includes a plurality of such molecules, and the like.

Introduction

The present invention is based, in part, on the discovery of a method for more accurately quantifying cfDNA, in particular chimeric cfDNA is a sample from a patient.

The methods of the invention comprise performing multiple PCR control reactions that result in at least two amplicons of different length (a "long" and a "short" amplicon) to control for the portion of DNA in a sample that can be amplified by PCR. The amplicons are generated by amplifying unique sequences present on the genome. The fraction of one (or both) of the amplicons obtained in the reaction is then used to determine the fraction of DNA that can be amplified by PCR, i.e., the fraction that can be amplified by a PCR of a desired length.

The method comprises performing a digital PCR on a cfDNA sample obtained from a patient. Typically, the cfDNA is isolated from blood, serum, or plasma. A digital PCR is performed that includes at least two amplification reactions to provide amplicons of a desired length where the two amplicons differ in length by at least 50 base pairs, and typically differ in length by at least 75 or 100 base pairs. Using the fractional abundance of one amplicon to assess the fractionation pattern, a factor can be calculated to correct for the amplifiable fraction of the PCR, i.e., the fraction that can be amplified by the diagnostic PCR that is being assessed in the analysis, to quantify the cfDNA concentration. The control two-length PCR reaction is performed separately on a cf DNA sample from the patient, typically prior to, a quantitative PCR for diagnosis, e.g., a SNP analysis to determine the status of a transplant organ, in a multiplex PCR.

The control PCR may further comprise a "spike-in" DNA, i.e., control DNA added to the stalling sample obtained from a patient, e.g., a blood, plasma, or serum sample, to control for the efficiency of extraction of the cfDNA from the patient sample.

Identification of Unique Sequences for Two-Length PCR Controls

A unique sequence is selected from the genome to serve as a target sequence for use to generate a long or a short amplicon as a control. The target unique sequence to generate the long amplicon is different from the target unique sequence that is used to generate the short amplicon. Any unique sequence on the genome may be used. The only criterion for selection is that the sequence is localized to a single locus and that amplification primers can be used to selectively amplify the unique sequence to provide an amplicon of a desired length.

The short and the long amplicons that are used to estimate the cfDNA that can be amplified by PCR typically vary by at least 100 bp or more in length. Typically the short amplicon is less than 150 base pairs, but greater than 30 base pairs in length, and the long amplicon is at least 150 base pairs in length and may be up to 250 or greater base pairs in length. Typically, the long amplicon is less than 600 base pairs in length and is frequently less than 400 or 300 base pairs in length.

Selection and design of primers to amplify a unique sequence to provide a control amplicon of desired length are well known to one of skill in the art. For example, PCR primers may be designed using standard primer design computer software techniques known to individuals skilled in the art. The variables considered during PCR primer design may include primer length, GC pair content, melting temperature, and size of the target nucleic acid amplified by the primer pair.

Amplification of DNA

Amplification reactions are performed on cfDNA obtained a sample, typically blood, serum, or plasma, from a patient. The amplification reactions performed in accordance with the invention comprise digital PCR.

Digital PCR is a technique where a limiting dilution of the sample is made across a large number of separate PCR reactions so that most of the reactions have no template molecules and give a negative amplification result. Those reactions that are positive at the reaction endpoint are counted as individual template molecules present in the original sample in a 1 to 1 relationship. (See, e.g., Kalina et al. NAR 25:1999-2004 (1997) and Vogelstein and Kinzler, PNAS 96:9236-9241 (1999); U.S. Pat. Nos. 6,440,706, 6,753,147, and 7,824,889; each incorporated by reference.) Quantitative partitioning is assumed, and the dynamic range is governed by the number of containers available for stochastic separation. The molecules are then detected by PCR and the number of positive containers is counted. Each successful amplification is counted as one molecule, independent of the actual amount of product. In some embodiments, a digital PCR may be a microfluidics-based digital PCR. In some embodiments, a droplet digital PCR may be employed.

The amplifiable fraction can be determined by assessing the amount of long or short amplicon obtained in the digital PCR. This can be calculated using any number of calculation parameters. In some embodiments, the amplicon size of the quantification PCR is used as an independent variable. For example, using 249 base pair and 93 base-pair amplicons:

$$D=0.043*Lamp^{(Li=0.15)}-0.093*sqrt(Lamp)+1.27$$

$$r^2=0.992 \quad \text{Equation 1}$$

$$\theta Amp=1.431D^4-3.931D^3+3.271D^2+0.129D+0.03$$

$$r^2=0.999 \quad \text{Equation 2}$$

A PCR on a cfDNA samples that provides a working range of between 25 and 200 base pairs for Lamp is typically considered to be acceptable for diagnostic evaluation of the cfDNA sample by using the equations given in the preceding paragraph.

Use of Controls with Diagnostic PCR

A control PCR in accordance with the invention for determining the amplifiable fraction of a cfDNA sample can be used with any number of diagnostic PCRs performed on sample to quantify chimeric (or mosaic) cfDNA. In some embodiments, the cfDNA sample is from a transplant patient that is to be analyzed for the presence, or proportion, of DNA in the sample that originates from a graft donor (see, e.g., PCT/US2014/040055, which is herein incorporated by reference). In some embodiments, the cfDNA is a maternal cfDNA sample to evaluate fetal DNA. In some embodiments, the cfDNA is from a cancer patient that is to be analyzed for the presence, or proportion, of DNA in the sample that originates from the malignant cells.

A "patient" in the context of this invention is any individual that is to be evaluated using a diagnostic cfDNA assay. In typical embodiments, the patient is a human. In other embodiments, the patient is a mammal, e.g., a murine, bovine, equine, canine, feline, porcine, ovine, caprine, or a primate.

Computer Analysis

In some embodiments, the present invention provides systems related to the above methods of the invention. In one embodiment the invention provides a system for analyzing circulating cell-free DNA, comprising: (1) a sample analyzer for executing the method of analyzing cf DNA in a patient's blood, serum or plasma using a two-length PCR to calculate the amplifiable fraction of a cfDNA sample as described above; (2) a computer system for automatically receiving and analyzing data obtained in step (1) to provide a correction factor to calculate the fraction of amplifiable DNA in the cfDNA.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 8, Windows™ 7, Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming, language/structured query language (PL/SQL), and the like. Java™- or JavaScript™-enabled browsers such as HotJava™ or Microsoft™ Explorer™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out the analysis and correlating functions as described above. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

EXAMPLES

The following examples are provided by way of illustration only and not by way of limitation. Those of skill in the art will readily recognize a variety of non-critical parameters that could be changed or modified to yield essentially similar results.

The following examples describes the development of an improved quantitative cfDNA assay.

Patients, Material and Methods

Blood samples from 43 patients after liver transplantation (LTx) were analyzed in this example. This analysis also employed samples from healthy volunteers that were obtained with informed consent. EDTA-whole blood (Sarstedt, Nümbrecht, Germany) was drawn and processed within 4 hours and stored frozen at −80° C. until extraction. For LTx patients, cfDNA tubes (9 mL Cell-Free DNA™ BCT, Streck Inc., Omaha, Nebr.) were used. LTx patient samples were drawn under an institutional review board-approved protocol with informed consent.

cfDNA Extractions

Before extraction, all plasma samples were centrifuged at 4000×g for 20 min at 4° C. cfDNA was extracted using Roches High Pure Viral Extraction Large Volume (LV) Kit (ROCHE LV, Roche Applied Science, Mannheim, Germany).

Fragment Size Measurement and Correction

The size distribution of multiple cfDNA samples was estimated using an BioAnalyzer 2000 with the high sensitivity DNA kit (Agilent, Waldbronn, Germany). The DNA content of each distinct peak was determined using the device software, the distribution within each peak was calculated after digitizing the electropherograms in intervals (min 10/peak). Generally, three distinct peaks are regularly observed in human cfDNA resembling the first three shortest moieties of apoptotic DNA fragmentation. The general formula to correct for the amplifiable template fraction ($\theta_{Amp}$) of any given amplicon length and template length is (FIG. 1):

$$DNA_{length\ corrected} = DNA_{measured} \frac{\text{Template length}}{\text{template length} - \text{amplicon length}}$$

The range of observed distributions was used to estimate the $\theta_{Amp}$ in cfDNA, by iterative modeling of cfDNA profiles in R.

R simulation 1: Simulations of cfDNA profiles for PCR amplification efficiency. Simulations of cfDNA profiles were calculated in R statistical programming language (http address www.r-project.org/). The extremes of the simulation were set to those that have been observed by capillary electrophoretic separations of plasma DNA. Parameters were as follows: First peak: size as 180 bp±20 (relative amount: 33 to 99%), second peak: size as 360 bp±30 (relative amount: 5 to 50%), third peak: size as 560 bp±40 (0 to 33%). Peaks were assumed to be Gaussian distributed with the given parameters. The three peaks were concatenated into one cfDNA profile and the amplifiable fraction θAmp was calculated according to the formula given in the text.

Five different probe-based assays with variable amplicon lengths were used to determine the concentration [cp/20 µL] of 10 ng sheared gDNA, native gDNA and cfDNA extracted from plasma of healthy volunteers. In order to correct the results obtained for the five different amplicon lengths, when performed on sheared DNA, the used sheared DNA was subjected to capillary electrophoresis and a model was fitted to the observed curve shape. The computed theoretic $\theta_{Amp}$ was used to correct the 5 lengths ddPCRs. The $\theta_{Amp}$ correction factors used for cfDNA were derived from the cfDNA profile simulations.

Fragmentation Profiling by ddPCR

Figure 2:
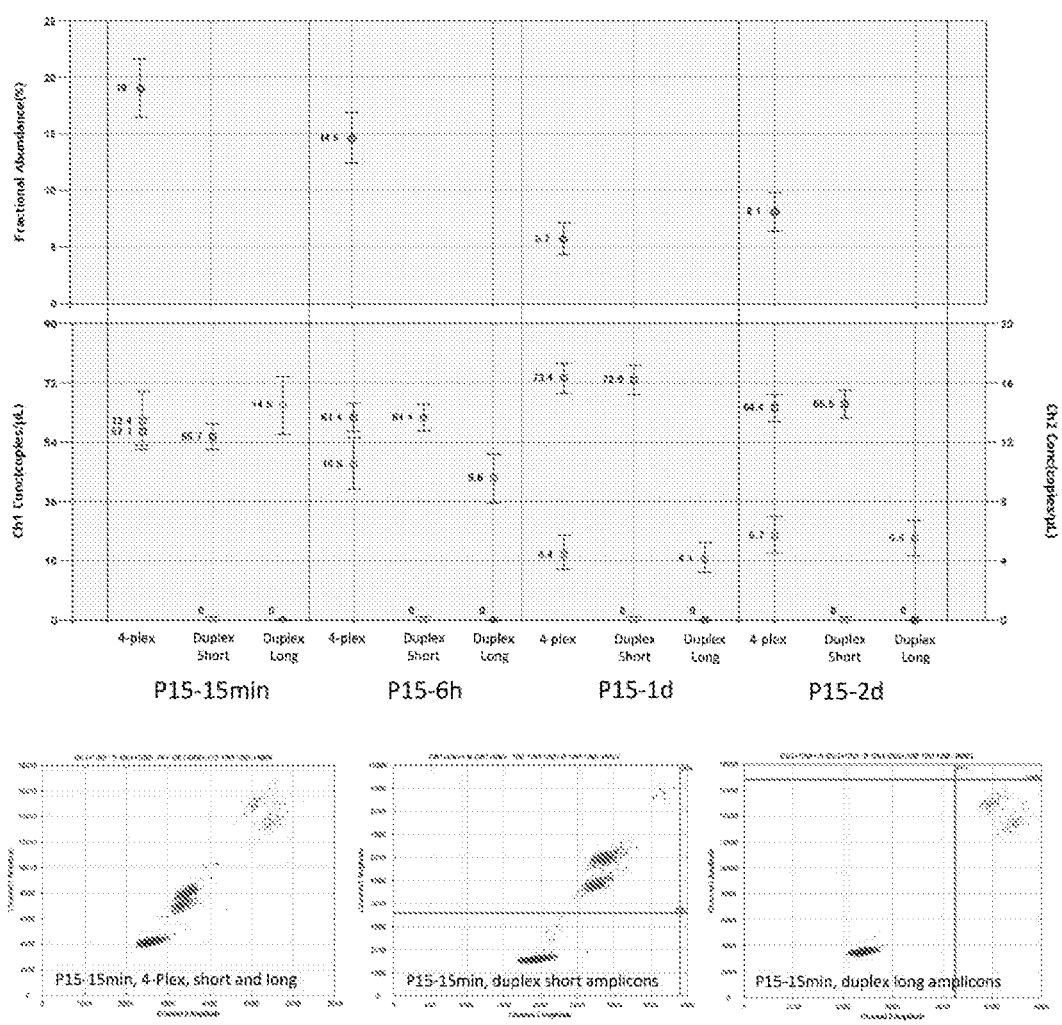
FIG. 2: Optimization of EvaGreen assay with four different amplicons. Reactions contained two short amplicons that produce a lower fluorescence signal than the two long amplicons, due to the lower EvaGreen intercalation. The upper panel shows the fractional abundance of the two long amplicons. These values represent the ddPCR-LI, which is used for correcting the concentration ddPCR for template versus amplicon size. The middle panel shows the cp/µL as calculated by Poisson statistics. Every sample was run in the final 4-plex assay as well as in two duplex reactions that either contained only the short amplicon primers or only the long amplicon primers. 4-plex results are not significantly different from 2-plex results. Lower panel: Examples of 2D-Plots of fluorescence signal obtained for the 4-plex and the two duplex reactions. The primers for the two short amplicons were added in slightly lower concentration (0.1 µmol/L) as for the two longer amplicons (0.15 µmol/L) in order enhance the separation of droplets containing two short amplicons versus droplets with one long amplicon. This was necessary to ensure that the droplet fraction that contains two short templates is still distinguishable from the droplet fraction containing one long amplicon. Furthermore, the 4-plex assay should not contain more than 1000 haploid genome equivalents (translating into approximately 4000 positive droplets) to allow unambiguous discrimination of polyclonal droplets.

A length index (ddPCR-LI) of cfDNA was assessed by a four-plex ddPCR performed in 20 µL of 1× QX200 ddPCR EvaGreen Supermix. In order to increase the number of positive droplets two short amplicons (92 bp and 94 bp) and two long amplicons (248 bp and 250 bp) were combined. See FIG. 2 for details of assay with four different amplicons. ddPCR-LI was defined as fractional abundance of the long amplicons. A broad range of cfDNA profiles was simulated as above; ddPCR-LI were calculated and recorded together with the $\theta_{Amp}$ of quantification ddPCR and used to model the dependency of the quantification correction factor $\theta_{Amp}$ from cfDNA profiles estimated using ddPCR-LI.

Results

Error Consideration: Correction for Amplicon Versus Template Length

Figure 3:
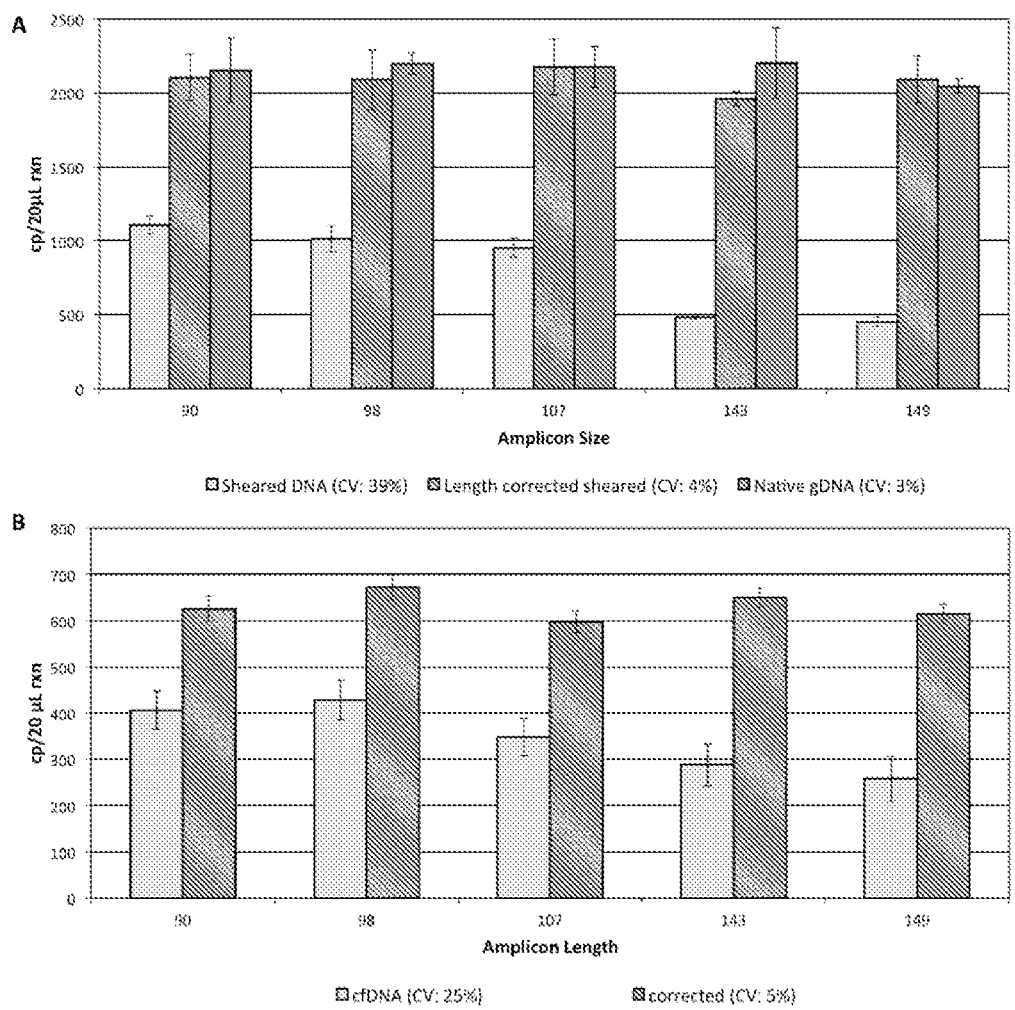
FIG. 3: A: The concentrations of a sheared gDNA and native gDNA were determined by five different ddPCR assays with varying amplicon length. The mean size of the sheared gDNA was 176 bp. The length distribution was determined by digitizing the Bioanalyzer electropherogram and the area under the curve was used to calculate the length correction factor for each amplicon length. After correction, the CV was reduced from 39% in the original measurement to 4%. B: The same five assays were run on one cfDNA sample and the correction factors were derived from a cfDNA profile based model. The CV could be reduced from 25% to 5% by correcting for amplicon versus template length.

In order to evaluate the influence of randomly fragmented template and amplicon length on assay performance, five different probe-based assays were used to quantify a sheared gDNA sample versus the same amount of native gDNA. The concentrations measured in the sheared DNA are strongly dependent on the amplicon length. The variability between the assays and underestimation of DNA-concentrations was removed by correcting the measured concentrations for amplicon and template length (FIG. 3), using a $\theta_{Amp}$ factor computed from a fit-model of the length profile. When cfDNA was used as template the length correction reduced the CV from 25% to 5%; here the factors are derived form a cfDNA profile based model.

Length Index of cfDNA Measured by ddPCR

Figure 4:
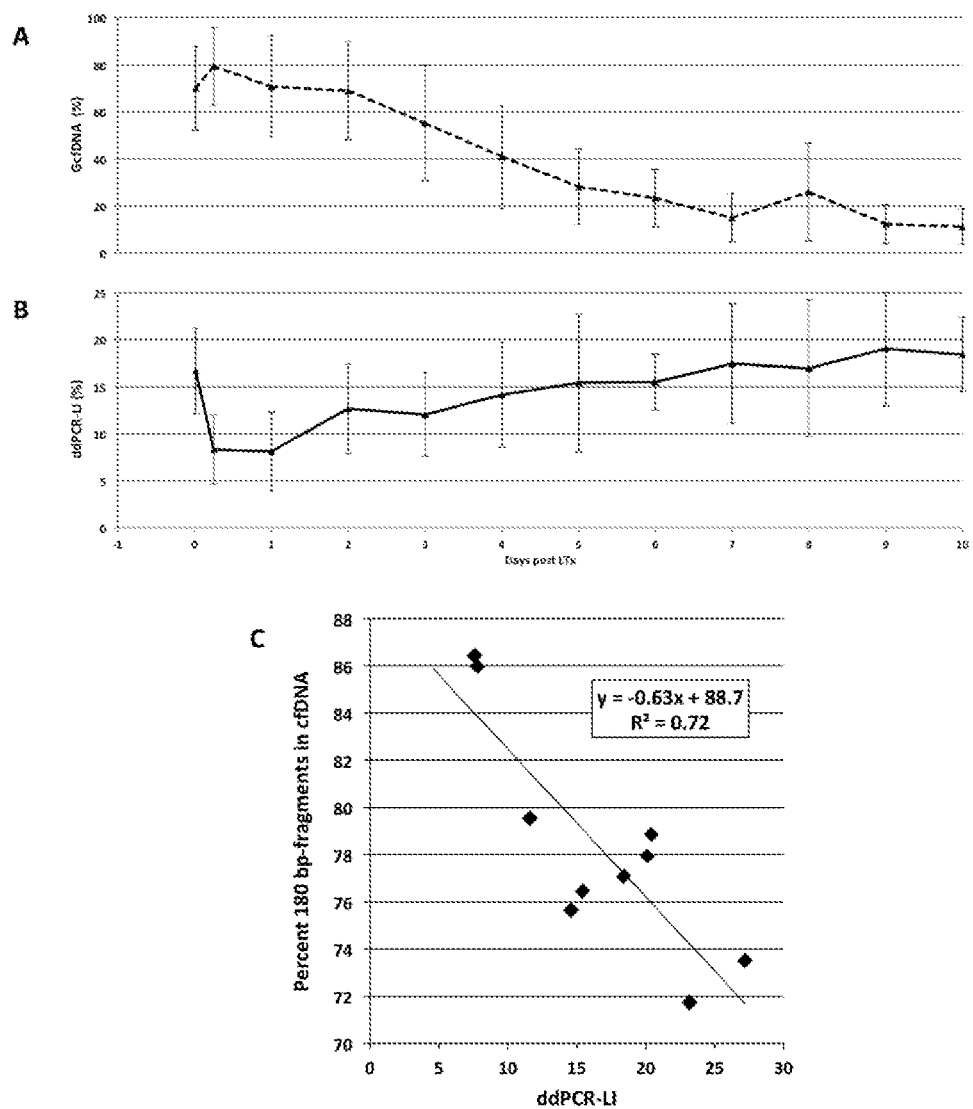
FIG. 4: A: Time-course of GcfDNA percentages B: Time-course of cfDNA length index ddPCR of the same samples as shown in A. The sharp drop of the cfDNA-LI at 6 h and 24 h after reperfusion is caused by the successive fragmentation of the graft-derived cfDNA fragments from high-molecular weight into dinucleosomal and finally into mononucleosomal stage (n=6 for time points: 15 min, 6 h, 6 d, 7 d, 10 d; n=5 for time points: 5 d, 8 d, 9 d, n=4 for time points: 24 h, 4 d; n=3 for time point: 2 d; n=2 for time point. C: The GcfDNA percentage is highly negatively correlated with the fractional abundance of larger sized amplicons as determined in the cfDNA length index ddPCR FIG. 5: A: Size distribution of cfDNA with several distributions; numbered: 1: second peak 1/15 of first; third peak 1/75 of first; 2: second peak 1/3 of first; third peak 1/3 of first; 3: second peak 1/1 of first; third peak 1/5 of first. B: Scatterplot of ddPCR-LI vs. $\theta_{Amp}$ of quantification amplicon as derived from simulations of a broad range of cfDNA fragmentation patterns. A second order polynome was fit to the data, which achieved a highly significant regression. C: A total of 210 samples from 39 LTx Patients from day 5 to day 377 post surgery were used for estimation of the difference between a mean correction and the ddPCR-LI-based correction of cfDNA content. The relative deviation defined as [concentration$_{(mean\ correction)}$−concentration$_{(LI\text{-}based\ correction)}$]/concentration$_{(LI\text{-}based\ correction)}$ is depicted. Dashed lines: 95% confidence interval borders, solid line: mean deviation. D: Concentrations as measured by QX100/200 (left) and the values after correcting for extraction efficiency (right) as percentage of the final value (after all corrections).

In most clinical plasma samples, the cfDNA size distribution resembles the apoptotic DNA ladder pattern, with three characteristic length fractions around 180 bp, 360 bp and 540 bp and with most molecules present in the 180 bp fraction. A ddPCR assay using the EvaGreen mastermix and amplicons of two different lengths (94 bp and 249 bp) was used to assess the size distribution of cfDNA fragments present in a particular sample. The ddPCR length index (ddPCR-LI) reflects the fractional abundance of the two longer amplicons and was first determined for a set of 10 cfDNA test samples for which the fragmentation profile was also determined using the Agilent Bioanalyzer. The ddPCR-LI was highly negatively correlated (r=−0.85) with the relative amount of total cfDNA (ng/µL) that was present in the shortest mononucleosomal fraction (FIG. 4). High ddPCR-LIs were detected immediately (15 min) after engraftment, indicative of necrotic graft DNA that emerged during cold ischemia. At 6 h after engraftment ddPCR-LI started to decrease and reached a minimum at 24 h. This minimum is explained by the dominating effect of the GcfDNA released during and immediately after surgery, after 24 h most of these fragments are degraded into the mononucleosomal fraction and thereby account for the low ddPCR-LI (FIG. 4).

Figure 5:
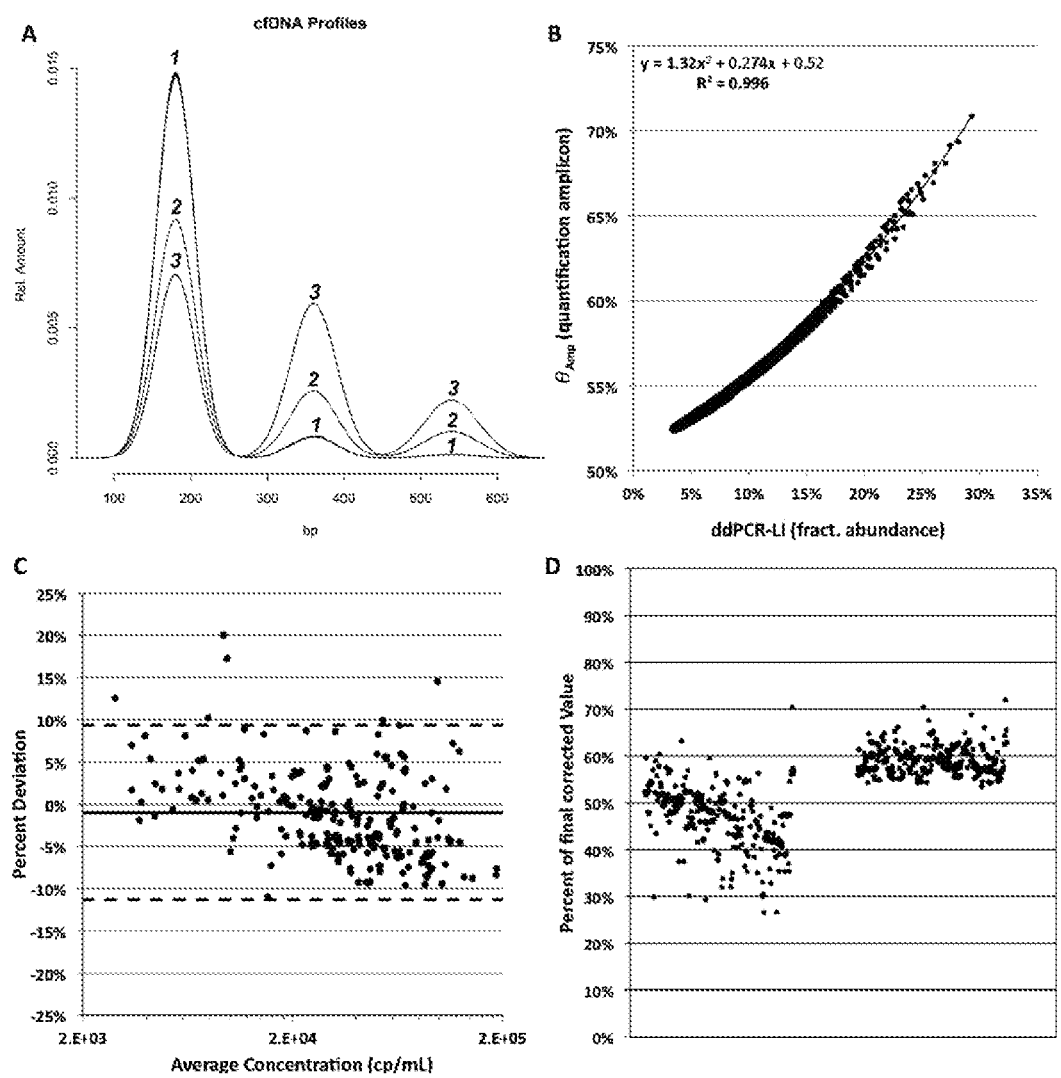

To use the ddPCR-LI for correction of PCR-yield $\theta_{Amp}$ of the quantification by ddPCR, cfDNA profiles were simulated and the ddPCR-LI was recorded in parallel with the amplifiable percentage of the short amplicons. FIG. 5 shows the range of simulated cfDNA profiles (A) and the resulting scatter of the data (B). The best fit of L-index with the specific $\theta_{Amp}$ was a second order polynome (Yield=1.32 ddPCR-LI$^2$+0.274 ddPCR-LI+0.515), which was used for further calculations.

The ddPCR-LI correction towards absolute copy number quantification was applied to a set of 210 cfDNA determinations of 39 liver recipients, compared to a fixed value of 59% for $\theta_{Amp}$ (derived from the mean LI of the sample set) used in the formula above. FIG. 5C shows the effect of that dynamic LI-based correction, from which it can be estimated that the error can be reduced by ±10% as deductible from the 1 standard deviation lines in the difference plot. The total effect of correcting for controllable molecule loss in the entire process is displayed in FIG. 5D. On average, the final cfDNA concentration after correction for both, extraction and $\theta_{Amp}$, which may be as close to the true values as achievable with reasonable efforts, is found to be 2.1-fold (95% CI: 1.7 to 3.3) higher than the raw concentrations given by the QX100/200.

This example thus illustrates the development and use of a two-length assay for quantifying digital PCR. The following steps of error control were applied for quantification: Extraction efficiency was controlled by use of a spike-in artificial DNA; Fragmentation pattern of cfDNA was assessed by a 2-length assay (ddPCR-LI) and used to assess the amplifiable fraction $\theta_{Amp}$; pre-amplification was compared with direct PCR to assess the inherent error.

The Roche and Qiagen extraction kits performed at 70-90% cfDNA recovery, which was corrected by the spike-in DNA. Different cfDNA fragmentation patterns occur in clinical samples contributing to ~20% imprecision, which is eliminated by ddPCR-LI derived $\theta_{Amp}$. Concentrations of cfDNA after correcting for these two effects were on average 2.1 fold (1.7 to 3.2) higher than raw values. Preamplification doubles the imprecision of results, the dead-volume of the QX200 (~40%) contributes to about 30% of the total error. Multiplex ddPCR assays for GcfNA without preamptification gave the most reliable results and quantities cfDNA traces of 0.25% with an imprecision of <10%.

This example demonstrates a reliable assay system to quantify low amounts of chimeric cfDNA, with total process control and minimized random error. Quantification bias was greatly reduced by taking measurable sources of inaccuracy into account.

All accession numbers, patents, patent applications, and other published reference materials cited in this specification are hereby incorporated herein by reference in their entirety for their disclosures of the subject matter in whose connection they are cited herein.

What is claimed is:

1. A method of quantifying chimeric cfDNA in a sample from a patient, the method comprising:
   (a) providing a cell-free DNA (cfDNA) sample from a blood, serum or plasma sample obtained from a patient;
   (b) performing a multiplex digital PCR comprising at least a first amplification and a second amplification on the cfDNA sample to determine a correction factor to correct for the degree of fragmentation in the cfDNA sample to provide the fraction of cfDNA that can be amplified for an amplified product of a defined size, wherein the first amplification targets a first single copy genomic locus in the patient genome and results in production of a first amplicon; and a second amplification targets a second single copy genomic locus in the patient genome and results in production of a second amplicon, wherein the first and second amplicon differ in length by at least 50 base pairs;

(c) determining the proportion of the first or the second amplicon in the total amplified product from the digital PCR of step (b) to provide the correction factor for the fraction of the cfDNA sample that can be amplified, and (d) correcting a diagnostic digital PCR performed on the cfDNA sample using the correction factor determined in step (c) to quantify the level of chimeric DNA.

2. The method of claim 1, wherein step (b) further comprises an amplification reaction that targets DNA that was added to the blood, serum, or plasma sample prior to extraction.

3. The method of claim 1, wherein the first and second amplicons differ in length by 100 nucleotides or more.

4. The method of claim 1, wherein the longer of the first and second amplicons is from 150 to 400 base pairs in length and the shorter of the first and the second amplicons is from 50 to 150 base pairs in length.

5. The method of claim 1, wherein the cfDNA sample is from a transplant patient.

6. The method of claim 1, wherein the cfDNA sample is from a cancer patient.

7. The method of claim 1, wherein the cfDNA sample is from a pregnant patient.

8. The method of claim 1, wherein the patient is a human.

* * * * *